United States Patent
Otsubo

(10) Patent No.: US 8,419,874 B2
(45) Date of Patent: Apr. 16, 2013

(54) METHOD FOR MAKING DIAPER

(75) Inventor: Toshifumi Otsubo, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 373 days.

(21) Appl. No.: 12/865,323

(22) PCT Filed: Dec. 16, 2008

(86) PCT No.: PCT/JP2008/072820
§ 371 (c)(1),
(2), (4) Date: Nov. 10, 2010

(87) PCT Pub. No.: WO2009/096106
PCT Pub. Date: Aug. 6, 2009

(65) Prior Publication Data
US 2011/0048617 A1    Mar. 3, 2011

(30) Foreign Application Priority Data

Jan. 30, 2008  (JP) ................................ 2008-019613

(51) Int. Cl.
*B32B 37/00* (2006.01)

(52) U.S. Cl.
USPC ........... 156/163; 156/160; 156/164; 156/229; 156/252; 156/257; 156/226

(58) Field of Classification Search .................. 156/160, 156/163, 164, 229, 252, 257, 226; 604/385.24, 604/385.27
See application file for complete search history.

(56) References Cited

U.S. PATENT DOCUMENTS

| | | | |
|---|---|---|---|
| 6,013,065 A * | 1/2000 | Suzuki et al. | 604/385.27 |
| 7,722,734 B2 * | 5/2010 | Otsubo | 156/226 |
| 2001/0023342 A1 * | 9/2001 | Suekane | 604/385.24 |

FOREIGN PATENT DOCUMENTS

| | | | |
|---|---|---|---|
| EP | 962207 A2 | * | 12/1999 |
| GB | 2268073 A | | 1/1994 |
| GB | 2268073 A | * | 1/1994 |
| JP | 6007725 U | | 2/1994 |
| JP | 6-327715 A | * | 11/1994 |
| JP | 2002011044 A | | 1/2002 |
| JP | 2003126143 A | | 5/2003 |
| JP | 2003-305080 A | * | 10/2003 |
| JP | 2003305080 A | | 10/2003 |
| JP | 2004000414 A | | 1/2004 |
| JP | 2007209522 A | | 8/2007 |

OTHER PUBLICATIONS

International Search Report for Application No. PCT/JP2008/072820 mailed Jan. 27, 2009.

* cited by examiner

*Primary Examiner* — Jeff Aftergut
(74) *Attorney, Agent, or Firm* — Lowe Hauptman Ham & Berner, LLP

(57) ABSTRACT

A method of making a diaper includes: forming the continuous sheet at a distance in a width direction from an imaginary center line M bisecting the width dimension of the continuous sheet with let-through openings for passage of feces at a regular pitch, bonding absorbent panels, each having an absorbent core to the middle section of a sheet piece having an area larger than the area of the absorbent core; coating the surface of the continuous sheet opposite to the surface to which the absorbent panels have been bonded with hot melt adhesive HM; and cutting the assembly of the continuous sheet and the absorbent panels along the imaginary vertical line V defined between each pair of the adjacent absorbent panels at the regular pitch to obtain the diapers.

7 Claims, 7 Drawing Sheets

METHOD FOR MAKING DIAPER

RELATED APPLICATIONS

The present application is a national phase of PCT/JP2008/072820 filed Dec. 16, 2008 and is based on, and claims priority from, Japanese Application No. 2008-019613, filed Jan. 30, 2008, the disclosure of which is hereby incorporated by reference herein in its entirety.

TECHNICAL FIELD

The present invention relates to a method for making a diaper and more particularly to a method for making a diaper having a capability to prevent urine and feces from being mixed with each other.

RELATED ART

PATENT DOCUMENT 1 discloses a diaper comprising a top-sheet, a back-sheet and an absorbent structure sandwiched between the top- and back-sheets wherein a skin-contact sheet is provided above the top-sheet. Longitudinally opposite ends of the top-sheet is bonded to the top-sheet and a section of this skin-contact sheet in a crotch region of the diaper is formed with a let-through opening wherein, around this opening, elastic member is attached under tension to the skin-contact sheet. In this diaper of prior art, feces discharged by a wearer is guided to pass this opening into a void space defined between the skin-contact sheet and the top-sheet. In consequence, the wearer's skin might not be soiled with body waste and developments of skin troubles such as a skin irritation can be avoided.

PATENT DOCUMENT 1: Japanese Patent Application Laid-Open Publication No. 2002-11044 (Claim 1 and FIG. 1)

DISCLOSURE OF THE INVENTION

Problem to be Solved by the Invention

It is well known that a prevention of ammonia evolution is essential to avoid skin troubles. However, there is no description in the disclosure of PATENT DOCUMENT 1 suggesting that the skin-contact sheet has a function to prevent urine and feces from being mixed with each other.

In view of such a prior art, it is a principal object of the present invention to provide a method for a diaper improved so that the skin-contact sheet, i.e., a sheet adapted to protect the wearer's skin from being soiled with body waste may function also to prevent an intermixture of urine and feces.

Measure to Solve the Problem

The object set forth above is achieved, according to the present invention, by an improvement in a method for making a disposable diaper from a continuous sheet of a chassis sheet having a desired width dimension, comprising steps of: forming the continuous sheet of the chassis sheet at a distance in a width direction from an imaginary center line bisecting the width dimension of the continuous sheet of the chassis sheet with let-through openings for passage of feces at a regular pitch, each of the let-through openings having a shape substantially symmetric about an imaginary vertical line extending orthogonally to the imaginary center line; bonding absorbent panels, each having an absorbent core previously bonded to a middle section of a sheet piece having an area larger than the area of the absorbent core and positioned so that the absorbent core may face the let-through opening for passage of feces and extend across the imaginary center line in the width direction so as to be substantially symmetric about the imaginary vertical line, to the continuous sheet of the chassis sheet along the outer peripheral edge of the absorbent core to provide an assembly of the continuous sheet of the chassis sheet and the absorbent panel; coating the surface of the continuous sheet of the chassis sheet opposite to the surface to which the absorbent panels have been bonded with hot melt adhesive so that the adhesive coated region may be defined between the imaginary center line and the let-through opening so as to be substantially symmetric about the imaginary vertical line; folding the continuous sheet of the chassis sheet in two along the imaginary center line with the surface coated with the hot melt adhesive inside and partially bonding the continuous sheet of the chassis sheet to itself; and cutting the assembly of the continuous sheet of the chassis sheet and the absorbent panels along the imaginary vertical line defined between each pair of the adjacent absorbent panels at the regular pitch to obtain individual diapers.

The present invention includes the following preferred embodiments:

an embodiment that the method further includes a step of forming the continuous sheet of the chassis sheet at a location opposite to the let-through opening for passage of feces about the imaginary center line and adapted to face the absorbent core with a let-through opening for passage of urine shaped substantially symmetric about the imaginary vertical line, an embodiment that the step of bonding the absorbent panels to the continuous sheet of the chassis sheet includes a sub-step of bonding a marginal region of the sheet piece extending outward beyond the peripheral edge of the absorbent core to the chassis sheet web, an embodiment that the step of bonding the absorbent panels to the continuous sheet of the chassis sheet includes a sub-step of bonding a region of the absorbent panel occupied by the absorbent core to the surface of the continuous sheet of the continuous sheet of the chassis sheet to which the absorbent panel is bonded along the imaginary center line, an embodiment that the method further includes a step of forming the continuous sheet of the chassis sheet between each pair of the adjacent let-through openings for passage of feces formed at the regular pitch with leg-openings corresponding to the leg-openings of the diaper at the regular pitch before the step of partially bonding the continuous sheet of the chassis sheet to itself, an embodiment that the method further includes a step of bonding waist-surrounding elastic members under tension to the opposite ends of the continuous sheet of the chassis sheet as viewed in the width direction before the step of partially bonding the continuous sheet of the chassis sheet to itself, and an embodiment that the method further includes a step of bonding leg-surrounding elastic members under tension to the peripheral edges of the leg-surrounding openings before the step of partially bonding the continuous sheet of the chassis sheet to itself.

EFFECT OF THE INVENTION

The diaper obtained by the method according to the present invention is, as will be described in details later, adapted to retain body waste in the void space formed within the diaper and to keep away the body waste from the wearer's skin. In this way, the wearer's skin is protected from being soiled with the body waste. Furthermore, a partition wall formed by partially bonding the chassis sheet web to itself serves to prevent an intermixing of urine and feces. In other words, the present invention provides a method for making the diaper wherein one and same sheet member functions to protect the wearer's skin from being soiled with body waste and at the same time functions to prevent the intermixing of urine and feces.

According to one embodiment of the present invention, the step of bonding the absorbent panels to the continuous sheet of the chassis sheet includes a sub-step of bonding a region of the absorbent panel occupied by the absorbent core to the surface of the continuous sheet of the chassis sheet to which the absorbent panel is bonded along the imaginary center line. This embodiment assures that the intermixing of urine and feces can be more reliably prevented.

Figure 1:
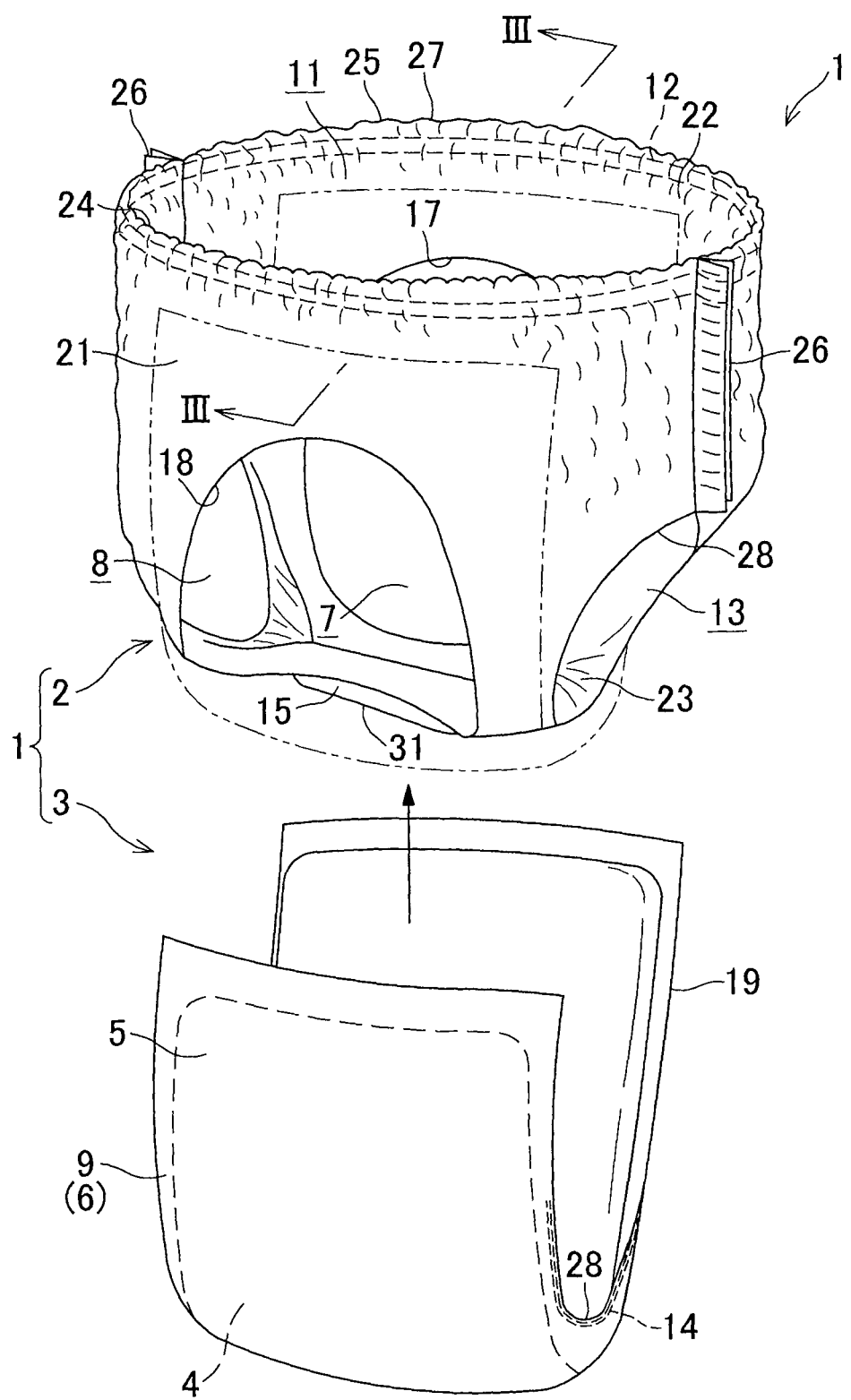
FIG. 1 is a perspective view of a diaper according to a first embodiment of the present invention.

IDENTIFICATION OF REFERENCE NUMERALS USED IN THE DRAWINGS 1 diaper
2 chassis sheet
3 absorbent panel
4 absorbent core
5 piece of sheet
6 outer periphery of absorbent core
7 let-through opening for passage of feces
8 let-through opening for passage of urine
9 marginal region
12 elastic members operatively associated with waist-opening
14 elastic members operatively associated with leg-openings
30 opposite ends of chassis sheet
113 leg-openings
M imaginary center line
V imaginary vertical line
M hot melt adhesive
W width direction

DETAILED DESCRIPTION OF THE PREFERRED EMBODIMENTS

Figure 3:
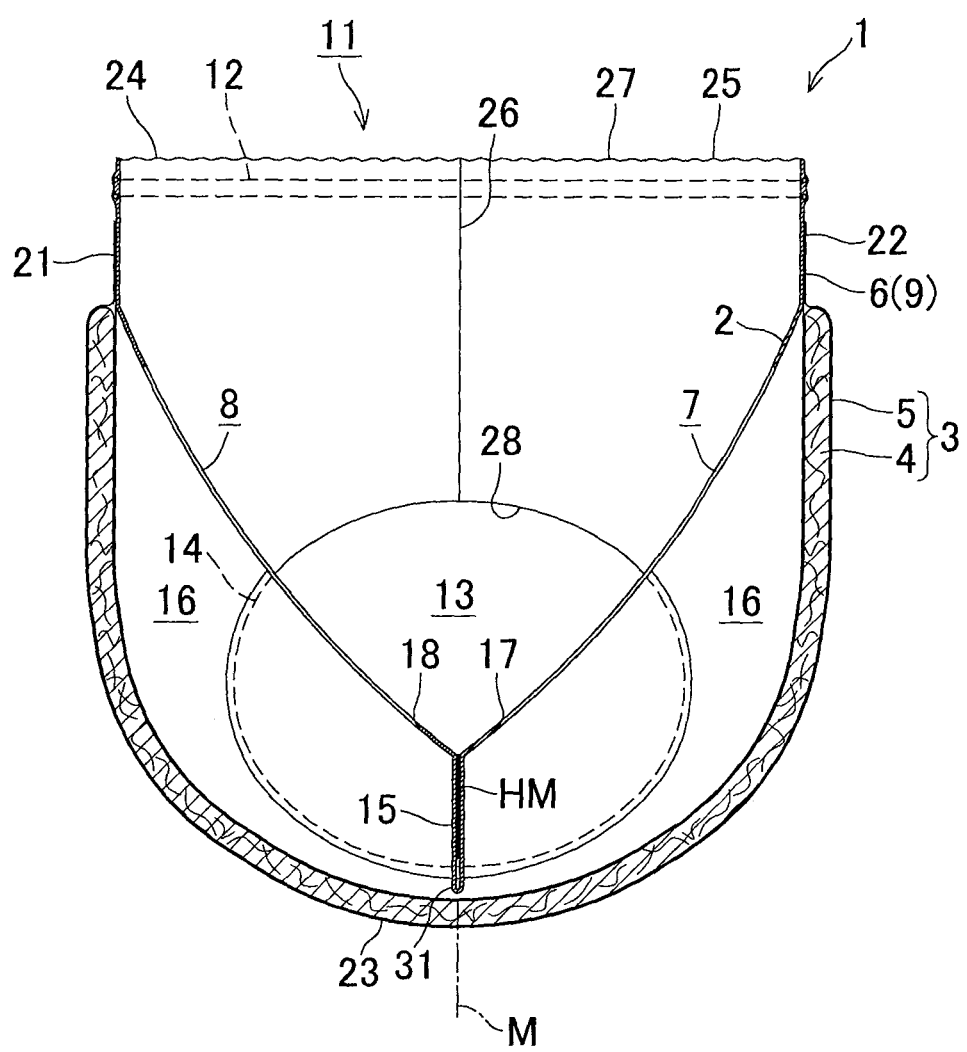
FIG. 3 is a sectional view taken along a line III-III in FIG. 1.
Figure 4:
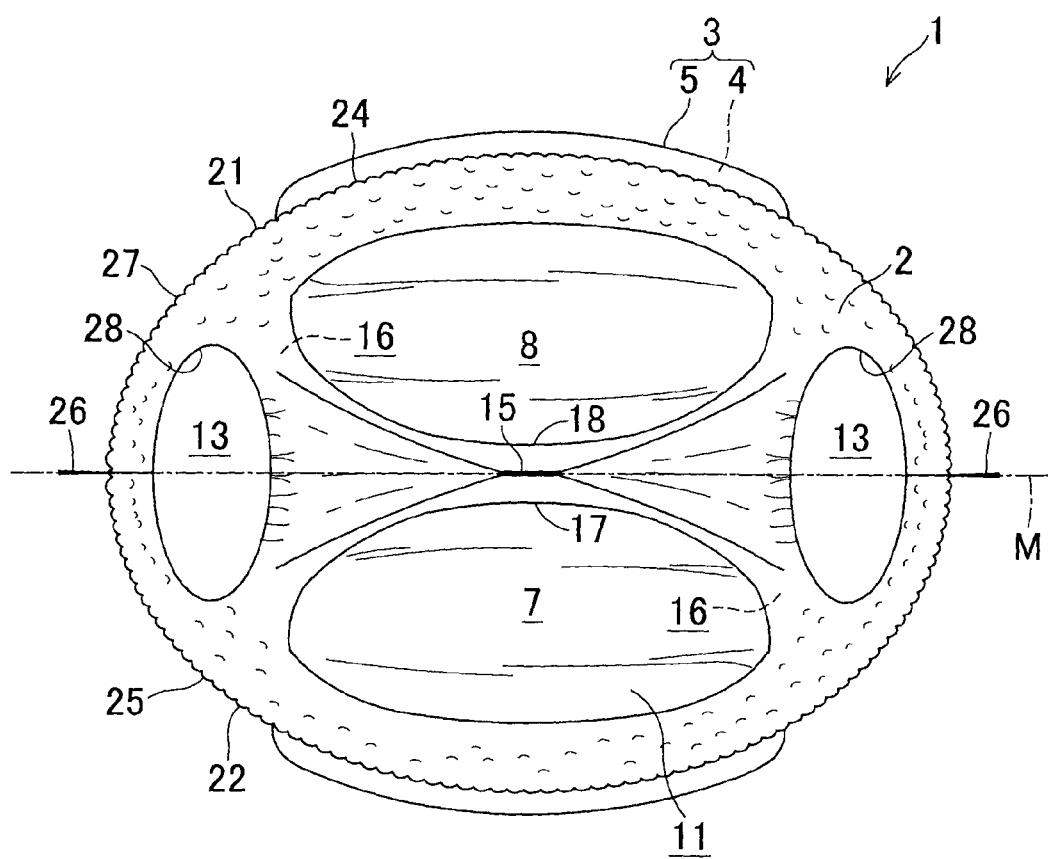
FIG. 4 is an overhead view of the diaper's inside as seen through the waist-opening.
Figure 5:
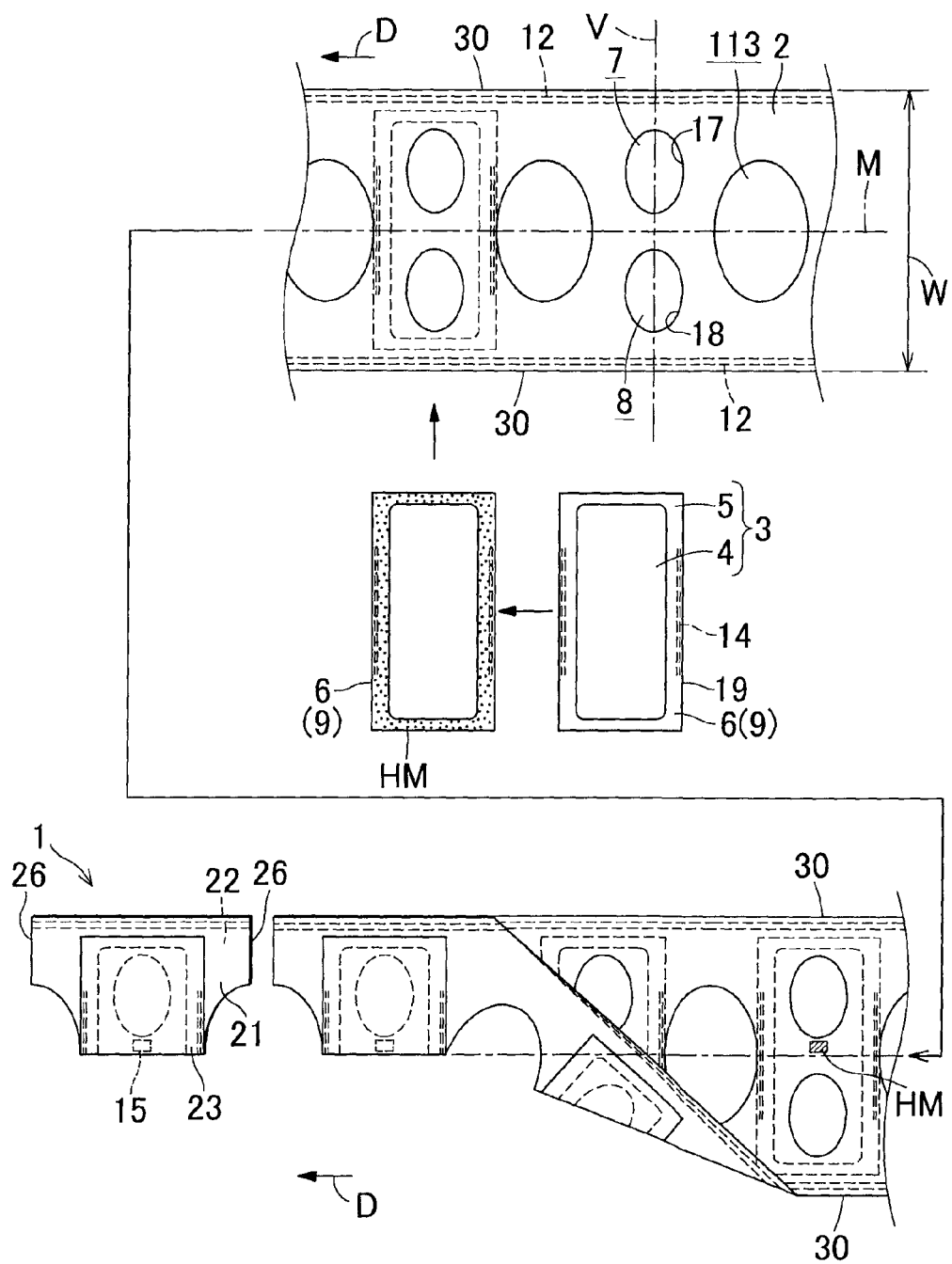
FIG. 5 is a schematic diagram illustrating a process for making the diaper.

Now the diaper 1 obtained by a method according to a first embodiment of the present invention and this method for making the diaper 1 will be described in details with reference to the accompanying drawings. FIG. 1 is an exploded perspective view of the diaper 1 obtained by this method, FIG. 2 is a plan view of the flatly developed diaper 1 as viewed from the side facing the wearer's skin, FIG. 3 is a sectional view taken along a line in FIG. 1 after the exploded components have been combined with each other again, FIG. 4 is an overhead view of the diaper's inside as seen through a waist-opening 11 and FIG. 5 is a schematic diagram illustrating a process for making the diaper 1.

Referring to FIG. 1, the diaper 1 basically comprises a chassis sheet 2 defining an outer shape of the diaper 1 and an absorbent panel 3. The chassis sheet 2 has a front waist region 21 adapted to come in contact with the wearer's ventral side, a rear waist region 22 adapted to come in contact with the wearer's dorsal side and a crotch region 23 extending between the front and rear waist regions 21, 22 and adapted to come in contact with the wearer's crotch region. The absorbent panel 3 is bonded to the surface of the chassis sheet 2 facing away from the wearer's skin so as to extend across the crotch region 23 into the front and rear waist regions 21, 22. With the diaper 1 put on the wearer's body, the absorbent panel 3 covers the wearer's crotch region. It should be understood that, hereinafter, the surface of the chassis sheet 2 adapted to come in contact with the wearer's skin will be referred to also as the inner surface and the surface of the chassis sheet 2 to which the absorbent panel 3 is bonded will be referred to also as the outer surface. A direction extending from the front waist region 21 across the crotch region 23 into the rear waist region 22 will be referred to hereinafter also as a longitudinal direction and a direction extending orthogonally to this longitudinal direction will be referred to hereinafter also as a transverse direction.

Figure 2:
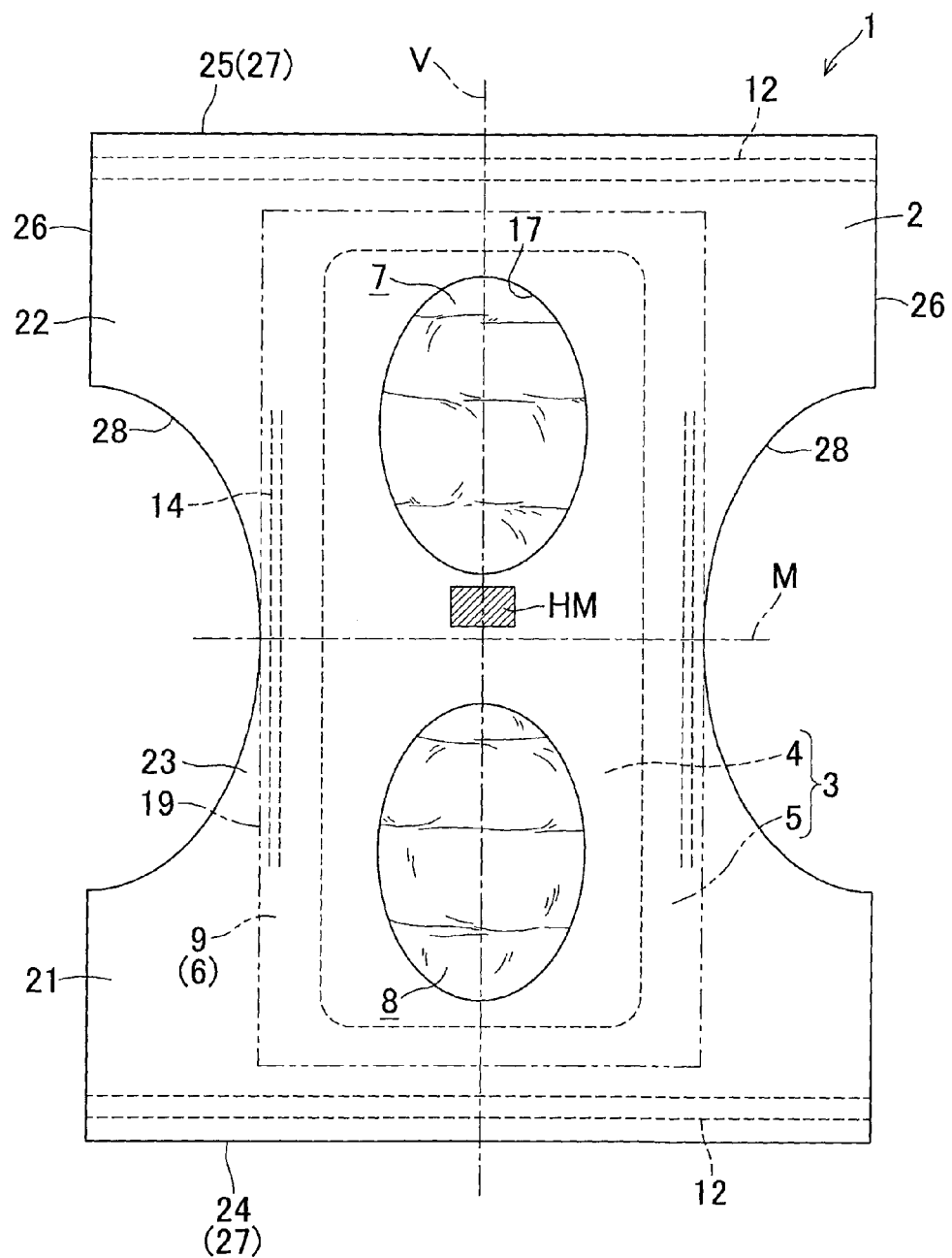
FIG. 2 is a plan view of the diaper as has been flatly developed.

Referring to FIG. 2, an outer periphery of the chassis sheet 2 comprises a front waist region's peripheral edge 24 and a rear waist region's peripheral edge 25 both extending in the transverse direction and a pair of chassis sheet's side edges 26, 26. Sections of the respective chassis sheet's side edges 26, 26 extending across the crotch region 23 concavely curve toward the middle of the chassis sheet 2. Sections of the chassis sheet's side edges 26, 26 extending in the front waist region 21 are joined to sections of the chassis sheet's side edges 26, 26 extending in the rear waist region 22 to obtain the pants-type diaper 1. Thereupon, the front waist region's peripheral edge 24 is connected to the rear waist region's peripheral edge 25 to form a waist-opening 11 and the concavely curving sections of the chassis sheet's side edges 26, 26 form a pair of leg-openings 13, 13. Waist-opening's peripheral edge 27 and leg-openings' peripheral edges 28 are provided with waist-surrounding elastic members 12 and leg-surrounding elastic members 14, respectively, attached under tension thereto. Alternatively, the chassis sheet 2 itself may be elasticized one in place of the elastic members 12, 14 to assure desired elasticity.

The absorbent panel 3 comprises a sheet piece 5 and an absorbent core 4 bonded thereto in a central region of the sheet piece 5. As the absorbent core 4, a bodily fluid-absorbent structure of well known arrangement, for example, an absorbent core formed by wrapping an absorbent material such as fluff pulp with a tissue paper may be used. The sheet piece 5 has an area larger than that of the absorbent core 4 and extends outward beyond the peripheral edge of the absorbent core 4. The absorbent core 4 has a sufficient area and an appropriate shape (e.g., rectangle, dumbbells etc.) to cover the crotch region of the wearer. The absorbent panel 3 may be formed by bonding the absorbent core 4 to a single sheet piece 5 or by sandwiching the absorbent core 4 between two or more sheet pieces 5.

According to the present embodiment, the absorbent panel 3 is smaller than the chassis sheet 2 in the longitudinal direction as well as in the transverse direction. Such absorbent panel 3 may be used to assure that the chassis sheet 2 concurrently functions as the skin-contact sheet disclosed in PATENT DOCUMENT 1. In consequence, a step of bonding the skin-contact sheet supplied from a production line separate from a production line of the chassis sheet 2 is unnecessary and a manufacturing process of the diaper 1 is correspondingly simplified.

At a location rather close to the rear waist region 22 with respect to an imaginary center line M bisecting the dimension between the front waist region's peripheral edge 24 and the rear waist region's peripheral edge 25, the chassis sheet 2 is formed in the crotch region 23 with a let-through opening 7 for passage of feces. At a location rather close to the front waist region 21, the chassis sheet 2 is formed in the crotch region 23 with a let-through opening 8 for passage of urine. However, the formation of the let-through opening 8 for passage of urine can be eliminated if the let-through opening 8 is not necessary.

The absorbent panel 3 is bonded to the outer surface of the chassis sheet 2 so that the absorbent core 4 bonded to the sheet piece 5 may properly face the let-through opening 7 for passage of feces and the let-through opening 8 for passage of urine. The outer periphery 6 of the absorbent core 4 constituting the absorbent panel 3 is bonded to the chassis sheet 2 by well known means such as a hot melt adhesive (not shown) or a heat sealing technique. Even when the let-through opening 8 for passage of urine is not formed, it is essential for the absorbent core 4 to be sufficiently large to extend across the imaginary center line M of the chassis sheet 2 so as to cover the crotch region 23 and to face the wearer's urethral orifice.

As has been previously described, the outer periphery 6 of the absorbent core 4 constituting the absorbent panel 3 is bonded to the chassis sheet 2. This means that the diaper 1 has a region in which the chassis sheet 2 and the absorbent core 4 can be spaced from each other. In this region, as shown in FIG. 3 by a sectional view, a void space 16 is formed between the absorbent core 4 of the absorbent panel 3 and the chassis sheet 2. This void space 16 is formed in the crotch region 23 of the diaper 1 in which the chassis sheet 2 is formed with the let-through opening 7 for passage of feces and the let-through opening 8 for passage of urine. Consequentially, with the diaper 1 put on the wearer's body, this void space 16 is formed in the wearer's crotch region and body waste having passed the let-through opening 7 for passage of feces and/or the let-through opening 8 for passage of urine is received in this void space 16 and kept away from the wearer's skin.

The chassis sheet 2 is tucked along the imaginary center line M of the chassis sheet 2 and this tucked portion is bonded together to form a partition wall 15. The partition wall 15 extends in the transverse direction within the void space 16 (See FIG. 4) and protrudes downward from the remaining section of the chassis 2 to the absorbent core 4 of the absorbent panel 3. In this way, the partition wall 15 serves to restrict an intermixing of the feces and the urine received in the void space 16. Specifically, the chassis sheet 2 functioning to protect the wearer's skin from being soiled with the body waste functions also to prevent the feces and the urine from being mixed together.

Referring to FIG. 4, when the inside of the diaper 1 is viewed from above through the waist-opening 11, the absorbent panel 3 can be seen below the let-through opening 7 for passage of feces and the let-through opening 8 for passage of urine across the void space 16. With the diaper 1 put on the wearer's body, the chassis sheet 2 comes in contact with the wearer's skin over a wide range and thereby protects the wearer's skin from being soiled with the body waste.

The chassis sheet 2 is tucked preferably at a distance from the let-through opening 7 for the passage of feces as well as from the let-through opening 8 for the passage of urine (See FIG. 3). It is possible thereby to prevent the peripheral edges of the let-through opening 7 for the passage of feces and the let-through opening 8 for the passage of urine from coming in contact with and irritating the wearer's skin.

Both the let-through opening 7 for the passage of feces and the let-through opening 8 for the passage of urine come in contact with the inner sides of the wearer's thighs and are thereby tightly closed. As a consequence, the body waste once retained in the void space might not leak out therefrom.

Now a method for making the diaper 1 will be described in detail with reference to FIG. 5. A continuous sheet of the chassis sheet 2 having a desired width dimension before cut into the individual chassis sheet 2 is continuously fed in a direction indicated by an arrow D from right to left as viewed in FIG. 5 and finally cut into the individual diapers 1. Opposite edges 30, 30 of the continuous sheet of the chassis sheet 2 correspond to the previously described front waist region's peripheral edge 24 and rear waist region's peripheral edge 25. The imaginary center line M bisecting the width dimension of the continuous sheet of the chassis sheet 2 in the direction orthogonal to the direction in which the continuous sheet of the chassis sheet 2 is fed corresponds to the previously described imaginary center line M of the diaper 1. A region extending in parallel to the imaginary center line M inclusive of this imaginary center line M corresponds to the crotch region 23 of the diaper 1 and regions extending on both sides of this region correspond to the front and rear waist regions 21, 22 of the diaper 1.

FIG. 5 illustrates a case in which the continuous sheet of the chassis sheet 2 has already been formed with leg-openings 113 corresponding to the leg-openings 13 of the diaper 1 at a regular pitch and the continuous sheet of the chassis sheet 2 has already been provided along the opposite edges 30, 30 with a plurality of waist-surrounding elastic members 12 attached under tension thereto. The term "regular pitch" used herein should be understood to be same as pitch at which the continuous sheet of the chassis sheet 2 is cut successively into the individual diapers 1 and depend on the dimension of the waist-opening 11 and, in other words, depend on so-called waist size of the diaper 1.

In regions defined at a distance from the imaginary center line M in the width direction, the continuous sheet of the chassis sheet 2 having a desired width dimension and continuously fed is formed with the let-through opening 7 for the passage of feces and the let-through opening 8 for the passage of urine by cutting out the continuous sheet of the chassis sheet 2 at the regular pitch. Both the let-through opening 7 and the let-through opening 8 are shaped to be substantially symmetric about an imaginary vertical line V which is orthogonal to the imaginary center line M. The let-through opening 7 and the let-through opening 8 are not limited to specific sizes and shapes so far as these openings 7, 8 can fulfill the expected functions and, for example, it is possible to form these openings 7, 8 in circular or oval shapes which are symmetric about the imaginary center line M. By shaping the let-through opening 7 and the let-through opening 8 symmetrically about the imaginary center line M in this manner, a pulling force exerted along the arrow D on the continuous sheet of the chassis sheet 2 being fed can be substantially equalized about the imaginary center line M and thereby a shape stabilization effect of the continuous sheet of the chassis sheet 2 can be achieved. It should be appreciated here that the formation of the let-through opening 8 for passage of urine can be eliminated on a case-by-case basis.

Then, the absorbent panel 3 having been prepared in a production line separate from the production line depicted in FIG. 5 is bonded to the continuous sheet of the chassis sheet 2. The absorbent panel 3 comprises, as has been previously described, the absorbent core 4 bonded to the middle section of the sheet piece 5. The sheet piece 5 is folded in two along its opposite side edges 19, 19, respectively, and the leg-surrounding elastic members 14 attached under tension between the folded sheet piece 5. The absorbent panel 3 is positioned in the middle region defined between each pair of the adjacent leg-openings 113.

In the step of bonding the absorbent panel 3 to the continuous sheet of the chassis sheet 2, after the absorbent panel 3 is positioned so that the absorbent core 4 may extend across the imaginary center line M and face the let-through opening 7 and the let-through opening 8 symmetrically about the imaginary vertical line V, the absorbent panel 3 is bonded along the outer periphery 6 of the absorbent core 4 to the continuous sheet of the chassis sheet 2. The bonding of the absorbent panel 3 to the continuous sheet of the chassis sheet 2 can be carried out by well known means such as a hot melt adhesive HM or a heat sealing technique. In this step, the marginal region of the sheet piece 5 extending outward beyond the peripheral edge of the absorbent core 4 is preferably bonded to the continuous sheet of the chassis sheet 2. The region of the sheet piece 5 occupied by the absorbent core 4 also can be partially bonded to the chassis sheet web 2. More specifically, the outer periphery 6 of the absorbent core 4 comprises the marginal region 9 of the sheet piece 5 extending outward beyond the peripheral edge of the absorbent core 4 and the part of the region lying adjacent the marginal region 9 and occupied by the absorbent core 4.

In the step of bonding the marginal region 9 of the sheet piece 5 extending outward beyond the peripheral edge of the absorbent core 4 to the continuous sheet of the chassis sheet 2, the marginal region 9 is bonded preferably over its entire surface to the continuous sheet of the chassis sheet 2.

Then, the surface of the continuous sheet of the chassis sheet 2 opposite to the surface to which the absorbent panel 3 has been bonded (i.e., the face of the drawing in FIG. 5) is coated in a section defined between the imaginary center line M and the let-through opening 7 for the passage of feces and being substantially symmetric about the imaginary vertical line V with the hot melt adhesive HM. More specifically, this section coated with the hot melt adhesive HM in this step is defined within the region in which the continuous sheet of the chassis sheet 2 faces the absorbent core 4 and the continuous sheet of the chassis sheet 2 can be spaced upward from the absorbent core 4.

Preferably, the continuous sheet of the chassis sheet 2 is coated with the hot melt adhesive HM insofar as the hot melt adhesive HM does not extend to respective peripheral edges 17, 18 of the let-through opening 7 and the let-through opening 8. The range in which the continuous sheet of the chassis sheet 2 is coated with the hot melt adhesive HM may be limited in this manner to avoid a problem that the wearer's skin might be irritated by the chassis sheet 2, particularly the respective peripheral edges 17, 18 of the let-through opening 7 and the let-through opening 8 having stiffness increased due to application of the hot melt adhesive HM (See FIGS. 1 and 4).

Assumed that the let-through opening 8 is not formed, the continuous sheet of the chassis sheet 2 is coated with hot melt adhesive HM preferably within the region in which the continuous sheet of the chassis sheet 2 can be spaced upward from the absorbent core 4 and a distance from the imaginary center line M is smaller than the minimum distance between the peripheral edge 17 of the let-through opening 7 and the imaginary center line M. In this case, the hot melt adhesive HM may be applied in a region defined between the imaginary center line M and the peripheral edge 17 of the let-through opening 7 or on the side opposite to the let-through opening 7 about the imaginary center line M.

Now the continuous sheet of the chassis sheet 2 is folded in two along the imaginary center line M with the surface coated with the hot melt adhesive HM inside and then bonded to itself. As a consequence, the section coated with the hot melt adhesive HM forms the partition wall 15 shown in FIG. 3. The partition wall 15 serves to prevent the feces and the urine from being mixed together and the partition wall 15 does not come in a direct contact with the wearer's skin. Taking account of this, the hot melt adhesive HM may be in any one of various coating patterns usually adopted in relevant technical fields such as a dotted pattern and a spiral pattern and, if desired, an overall coating pattern may be adopted to make the stiffness of the partition wall 15 higher than in the remaining part of the chassis sheet 2. In addition, the continuous sheet of the chassis sheet 2 is coated with the hot melt adhesive HM in a range as wide as possible in the direction of the imaginary vertical line V insofar as the hot melt adhesive HM does not extend to the respective peripheral edges 17, 18 of the let-through opening 7 and the let-through opening 8 in order to form the partition wall 15 having a correspondingly large area.

After the step of partially bonding the continuous sheet of the chassis sheet 2 having been folded over to itself, the assembly of the continuous sheet of the chassis sheet 2 and the absorbent panels 3 are cut in the direction of the imaginary vertical line V between each pair of the adjacent absorbent panels 3 at the regular pitch to obtain the individual diapers 1. In this step, the opposite side edges 26 on the side of the front waist region 21 may be joined to the opposite side edges 26 on the side of the rear waist region 22 to obtain the pants-type diapers 1. Alternatively, the opposite side edges 26 on the side of the front waist region 21 and the opposite side edges 26 on the side of the rear waist region 22 may be provided with mechanical fasteners each comprising a loop member and a hook member to obtain an open-type diapers 1.

While the case in which the continuous sheet of the chassis sheet 2 previously formed with the leg-openings 113 has been described above, the method according to the present invention can be implemented so far as a step of forming the leg-openings 113 is carried out before the step of partially bonding the continuous sheet of the chassis sheet 2 to itself. For example, the step of forming the leg-openings 113 may be carried out after the step of bonding the absorbent panels 3 to the continuous sheet of the chassis sheet 2.

While a case in which the absorbent panels 3 previously provided with the leg-surrounding elastic members 14 has been described above, it is also possible to, after the leg-surrounding elastic members 14 have been attached under tension to the continuous sheet of the chassis sheet 2, bond the absorbent panels 3 to the continuous sheet of the chassis sheet 2 so as to cover the leg-surrounding elastic members 14 with the respective sheet pieces 5 of the absorbent panels 3.

Figure 6:
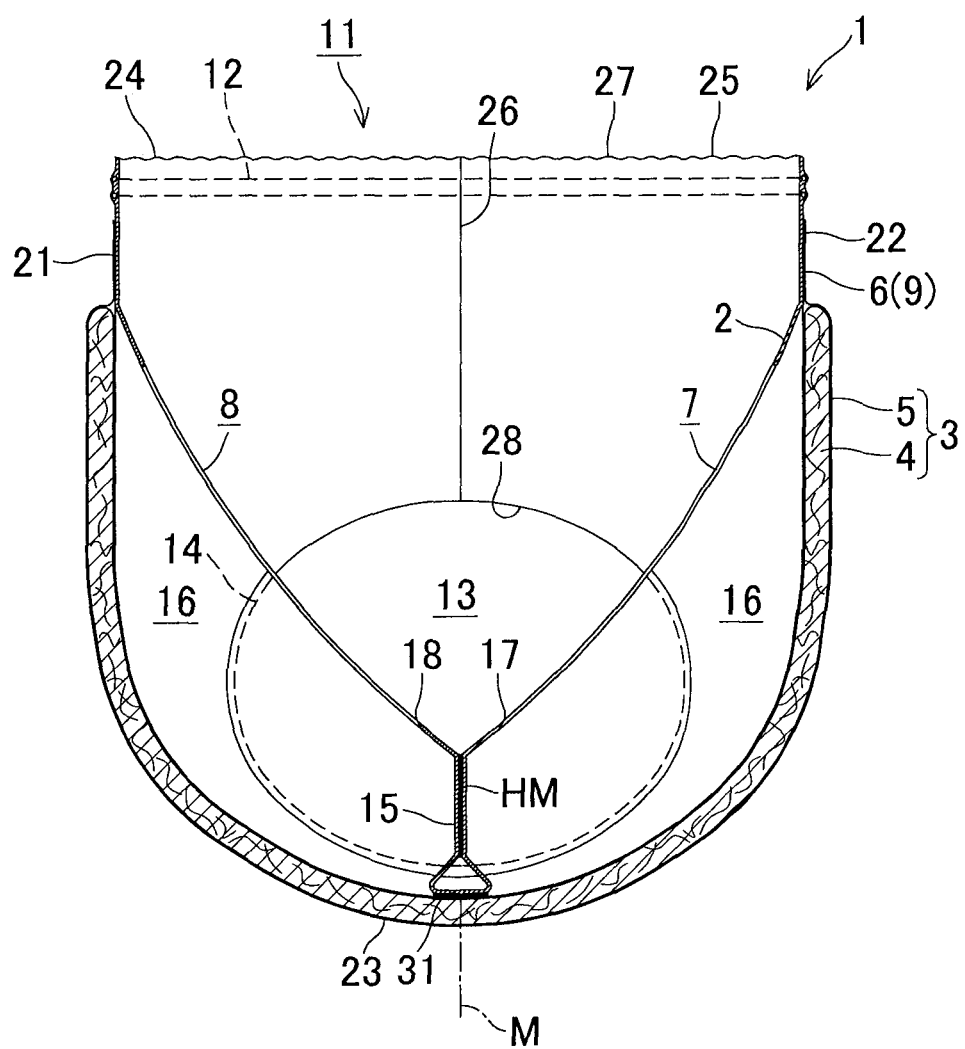
FIG. 6 is a sectional view of the diaper according to a second embodiment of the present invention.

Now the second embodiment will be described with reference to FIGS. 6 and 7. FIG. 6 is a sectional view similar to FIG. 3, showing the diaper 1 obtained by a method according to the second embodiment and FIG. 7 is a schematic diagram illustrating a process for making the diaper 1 according to the second embodiment.

Referring to FIG. 6, a lower edge 31 of the partition wall 15 closest to the absorbent panel 3 is bonded to the absorbent panel 3. The lower edge 31 lies on the imaginary center line M of the continuous sheet of the chassis sheet 2. The lower edge 31 of the partition wall 15 bonded to the absorbent panel 3 in this manner assures that an undesirable intermixing of the feces and the urine is further reliably prevented. The other features of the second embodiment are similar to those of the first embodiment and will not be repetitively described.

Figure 7:
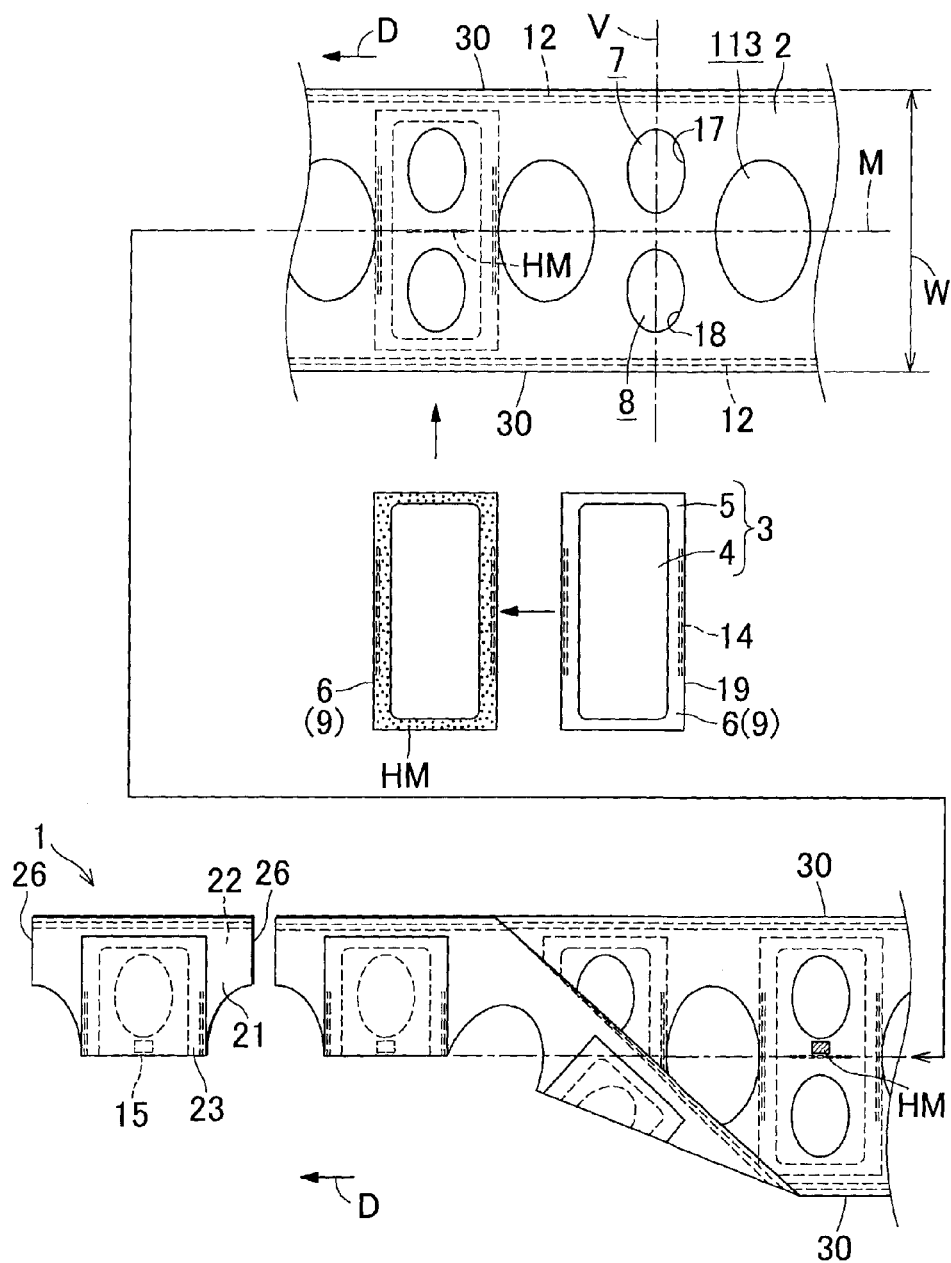
FIG. 7 is a schematic diagram illustrating a process for making the diaper according to the second embodiment of the present invention.

Referring to FIG. 7, a method for making the diaper 1 having the partition wall 15 of which the lower edge 31 is bonded to the absorbent panel 3 will be described below on the assumption that the continuous sheet of the chassis sheet 2 has previously formed with the leg-openings 113 corresponding to the leg-openings 13 at the regular pitch and the continuous sheet of the chassis sheet 2 is fed in the direction of the arrow D.

First, as illustrated on the right hand of FIG. 7, the let-through opening 7 and the let-through opening 8 are formed symmetrically about the imaginary vertical line extending orthogonally to the imaginary center line M. Then, the surface of the continuous sheet of the chassis sheet 2 to which the absorbent panels 3 will be bonded is coated along the imaginary center line M with the hot melt adhesive HM by means of which the absorbent panels 3 are bonded to the continuous sheet of the chassis sheet 2. In this step, the hot melt adhesive HM is preferably applied so as to be substantially symmetric about the imaginary vertical line V.

The range of coating the continuous sheet of the chassis sheet 2 with the hot melt adhesive HM by means of which the absorbent panels 3 are bonded to the continuous sheet of the chassis sheet 2 is not specified so far as dimension of applied the hot melt adhesive HM in the direction parallel to the imaginary center line M is smaller than the dimension of the region in which the continuous sheet of the chassis sheet 2 faces the individual absorbent cores 4.

In the case of the diaper for baby, for example, the dimension of the adhesive HM coated region as measured in the imaginary center line M is preferably in a range of 10 to 50 mm and more preferably in a range of 15 to 35 mm. This dimension set to 10 mm or less may cause a leak trouble and this dimension set to exceed 50 mm may cause another trouble such that the diaper becomes bulky in the crotch region of the wearer and this bulkiness often brings uncomfortable wearing conditions to the wearer.

The dimension as measured in the direction of the imaginary vertical line V is appropriately set so that a sufficiently high bonding strength to prevent the chassis sheet 2 and the absorbent panel 3 from being peeled off from each other when the diaper 1 is worn. Specifically, this dimension is preferably set to be in a range of 10 to 50 mm in the case of the diaper 1 for infant.

The location in the direction of the imaginary vertical line V at which the hot melt adhesive HM is applied in order to bond the absorbent panels 3 to the continuous sheet of the chassis sheet 2 is closer to the imaginary center line M than the location of the hot melt adhesive HM applied in order to bond the inner surface of the continuous sheet of the chassis sheet 2 partially to itself is.

Then in the step of bonding the absorbent panels 3 to the continuous sheet of the chassis sheet 2, each of the absorbent panels 3 is bonded along the outer periphery 6 to the continuous sheet of the chassis sheet 2 in a manner similar to that of the first embodiment. Then the absorbent panels 3 are bonded to the continuous sheet of the chassis sheet 2 on the imaginary center line M by means of the hot melt adhesive HM having been applied in the previous step. Following steps are also similar to those of the first embodiment. Specifically, the surface of the continuous sheet of the chassis sheet 2 opposite to the surface to which the absorbent panels 3 have been bonded is coated with the hot melt adhesive HM used for partially bonding the inner surface of the continuous sheet of the chassis sheet 2. The continuous sheet of the chassis sheet 2 is folded in two with the hot melt adhesive HM coated surface inside, then the respective halves of the continuous sheet of the chassis sheet 2 are partially bonded to each other and finally such assembly of the continuous sheet of the chassis sheet 2 and the absorbent panels 3 is successively cut to obtain the individual diapers 1 (See FIG. 6).

If the chassis sheet 2 sags when the diaper 1 is worn, the chassis sheet 2 may be displaced in the wearer's crotch region so as to interfere with the passage of urine and/or to bite into buttock cleavage. To avoid this, in the step of partially bonding the continuous sheet of the chassis sheet 2 to itself, the continuous sheet of the chassis sheet 2 is coated with the hot melt adhesive HM preferably in such a manner that the length dimension of the chassis sheet 2 in the region of the diaper 1 in which the chassis sheet 2 is free to be spaced upward from the absorbent core 4 in the direction of the imaginary vertical line V (i.e., the longitudinal direction of the diaper 1) as measured after bonding may be reduced to one-half or less of the length dimension before bonding. Thereby, the undesirable sag of the chassis sheet 2 can be avoided by a tension exerted on the chassis sheet 2 as the diaper 1 is worn.

In a specific example shown by FIG. 7, the continuous sheet of the chassis sheet 2 is coated with the hot melt adhesive HM so that the range extending in the imaginary vertical line V in which the continuous sheet of the chassis sheet 2 is partially bonded to itself may be 50% or more of the distance between the imaginary center line M and the peripheral edge 17 of the let-through opening 7 for passage of feces without extending to the peripheral edge 17 of the let-through opening 7, and thereafter the respective inner surface of the continuous sheet of the chassis sheet 2 folded in two may be partially bonded to each other.

In the first and second embodiments as have described above, as stock materials for the chassis sheet 2, the sheet piece 5 and the others, those usually used in relevant technical fields such as liquid-pervious or liquid-impervious fibrous non-woven fabrics or plastic films may be selectively used depending on regions in the diaper 1. It is also possible to combine two or more sheets to form the chassis sheet 2 and/or the sheet piece 5, for example, by using fibrous non-woven fabrics having elasticity in regions such as the waist-opening 11 and the leg-openings 13 of the diaper 1 to which elasticity is required and using inelastic fibrous non-woven fabrics in other regions to which no elasticity is required.

For example, it is possible to form the chassis sheet 2 by combining two or more sheets so that fibrous non-woven fabrics having elasticity may be used for the front and rear waist regions 21, 22 and inelastic fibrous non-woven fabrics may be used for the crotch region 23. Alternatively, it is possible to form the chassis sheet 2 by composite sheet comprising liquid-pervious and liquid-impervious non-woven fabrics laminated one upon another.

The invention claimed is:

1. A method of making diapers from a continuous sheet of a chassis sheet having a desired width dimension continuously fed, said method comprising:

forming said continuous sheet of said chassis sheet at a distance in a width direction from an imaginary center line bisecting said width dimension of said continuous sheet of said chassis sheet with let-through openings for passage of feces at a regular pitch, each of said let-through openings having a shape substantially symmetric about an imaginary vertical line extending orthogonally to said imaginary center line;

bonding absorbent panels, each having an absorbent core previously bonded to a middle section of a sheet piece having an area larger than the area of said absorbent core and positioned so that said absorbent core may face said let-through opening for the passage of feces and extend across said imaginary center line in said width direction so as to be substantially symmetric about said imaginary vertical line, to said continuous sheet of said chassis sheet web along the outer peripheral edge of said absorbent core to provide an assembly of said continuous sheet of said chassis sheet and said absorbent panels;

coating the surface of said chassis sheet web opposite to the surface to which said absorbent panels have been bonded with hot melt adhesive so that the adhesive coated region may be defined between said imaginary center line and said let-through opening so as to be substantially symmetric about said imaginary vertical line;

folding said continuous sheet of said chassis sheet in two along said imaginary center line with said surface coated with the hot melt adhesive inside and partially bonding said continuous sheet of said chassis sheet to itself; and cutting said assembly of said continuous sheet of said chassis sheet and said absorbent panels along said imaginary vertical line defined between each pair of the adjacent absorbent panels at said regular pitch to obtain said diapers.

2. The method defined by claim 1 further including a step of forming said continuous sheet of said chassis sheet at a location opposite to said let-through opening for the passage of feces about said imaginary center line and adapted to face said absorbent core let-through openings for passage of urine with a let-through opening for passage of urine shaped substantially symmetric about said imaginary vertical line.

3. The method defined by claim 1, said step of bonding said absorbent panels to said continuous sheet of said chassis sheet includes a sub-step of bonding a marginal region of said sheet piece extending outward beyond the peripheral edge of said absorbent core to said continuous sheet of said chassis sheet.

4. The method defined by claim 1, said step of bonding said absorbent panels to said continuous sheet of said chassis sheet includes a sub-step of bonding the region of said absorbent panel occupied by said absorbent core to the surface of said continuous sheet of said chassis sheet to which said absorbent panel is bonded along said imaginary center line.

5. The method defined by claim 1 further including a step of forming said continuous sheet of said chassis sheet between each pair of the adjacent let-through openings for the passage of feces formed at said regular pitch with leg-openings corresponding to the leg-openings of the diaper at said regular pitch before said step of partially bonding said continuous sheet of said chassis sheet to itself.

6. The method defined by claim 1 further including a step of bonding waist-surrounding elastic members under tension to opposite ends of said continuous sheet of said chassis sheet as viewed in the width direction before said step of partially bonding said continuous sheet of said chassis sheet to itself.

7. The method defined by claim 6 further including a step of bonding leg-surrounding elastic members under tension to peripheral edges of said leg-surrounding openings before said step of partially bonding said continuous sheet of said chassis sheet to itself.

* * * * *